US006183505B1

(12) United States Patent
Mohn, Jr. et al.

(10) Patent No.: US 6,183,505 B1
(45) Date of Patent: Feb. 6, 2001

(54) METHOD OF STENT RETENTION TO A DELIVERY CATHETER BALLOON-BRAIDED RETAINERS

(75) Inventors: Michael A. Mohn, Jr., San Diego; Mark L. Stiger, El Cajon; David J. Lentz, La Jolla; Rey O. Cruz, National City, all of CA (US)

(73) Assignee: Medtronic AVE, Inc., Santa Rosa, CA (US)

( * ) Notice: Under 35 U.S.C. 154(b), the term of this patent shall be extended for 0 days.

(21) Appl. No.: 09/266,113

(22) Filed: Mar. 11, 1999

(51) Int. Cl.[7] .................................................. A61F 2/06
(52) U.S. Cl. .................................................. 623/1.11
(58) Field of Search .................................. 606/108, 192, 606/194, 198; 604/104; 623/1.11

(56) References Cited

U.S. PATENT DOCUMENTS

| 3,902,501 | | 9/1975 | Citron et al. . | |
|---|---|---|---|---|
| 4,950,227 | | 8/1990 | Savin et al. . | |
| 5,108,416 | | 4/1992 | Ryan et al. . | |
| 5,480,423 | | 1/1996 | Ravenscroft et al. . | |
| 5,522,883 | | 6/1996 | Slater et al. . | |
| 5,549,635 | | 8/1996 | Solar . | |
| 5,591,222 | * | 1/1997 | Susawa et al. | 606/195 |
| 5,643,278 | | 7/1997 | Wijay . | |
| 5,653,689 | * | 8/1997 | Buelna et al. | 604/104 |
| 5,683,451 | | 11/1997 | Lenker et al. . | |
| 5,700,243 | * | 12/1997 | Narciso, Jr. | 606/194 |
| 5,725,549 | | 3/1998 | Lam . | |
| 5,746,745 | | 5/1998 | Abele et al. . | |
| 5,776,141 | | 7/1998 | Klein et al. . | |
| 5,807,398 | * | 9/1998 | Shaknovich | 606/108 |
| 5,810,871 | | 9/1998 | Tuckey et al. . | |
| 5,891,154 | * | 4/1999 | Loeffler | 606/108 |
| 5,935,135 | * | 8/1999 | Bramfitt et al. | 606/108 |
| 5,980,530 | * | 11/1999 | Willard et al. | 606/108 |

FOREIGN PATENT DOCUMENTS

| 0 442 657 A2 | 8/1991 | (EP) . |
|---|---|---|
| WO 96/31249 | 10/1996 | (WO) . |
| WO 97/07756 | 3/1997 | (WO) . |
| WO 97/07388 | 2/1998 | (WO) . |
| WO 98/07390 | 2/1998 | (WO) . |

\* cited by examiner

Primary Examiner—Gene Mancene
Assistant Examiner—Eduardo C. Robert
(74) Attorney, Agent, or Firm—Sterne, Kessler, Goldstein & Fox P.L.L.C.

(57) ABSTRACT

A stent delivery balloon catheter system includes a pair of retainers which are anchored to the catheter to hold the stent against the balloon until the stent is to be deployed. Each retainer is made of filaments which are woven together to form a braided tube shaped structure. Further, each retainer has one end which is anchored to the catheter while the free end of the retainer overlaps a respective end of the stent. Upon inflation of the balloon for deployment of the stent, the balloon also urges against each retainer. This causes the woven tube structure of the retainer to expand, and thereby shorten. As the retainers shorten, they also withdrawn from the stent, and thereby release the stent for deployment.

20 Claims, 5 Drawing Sheets

METHOD OF STENT RETENTION TO A DELIVERY CATHETER BALLOON-BRAIDED RETAINERS

FIELD OF THE INVENTION

The present invention pertains generally to stent delivery catheters. More particularly, the present invention pertains to stent retainers which are incorporated into a stent delivery system for the purpose of holding a stent against the balloon of a balloon catheter during its advancement into the vasculature of a patient. The present invention is particularly, but not exclusively, useful as a stent retainer which relies on a mechanical reconfiguration of the retainer to separate the retainer from the stent during its deployment.

BACKGROUND OF THE INVENTION

The introduction of a foreign object into the vasculature of a patient presents obviously complex problems. Specifically, both the object and its delivery system must be capable of being advanced into the vasculature for its intended purpose, without unduly traumatizing the patient. Further, this advancement must be accomplished accurately and with great precision. To this end, interventional systems are typically designed to be as smooth as possible, to have as small a profile as possible, and to be as easily controlled as possible. These design characteristics, however, do not directly address the different set of problems which are confronted when, after being advanced into the vasculature by a delivery system, an object is thereafter deployed or disengaged from the delivery system to remain in situ.

In order to deploy or disengage an object from a delivery system in the vasculature of a patient, it is necessary to somehow reconfigure the object and the delivery system for this purpose. The structures used for these functions, however must not be allowed to interfere with the aforementioned task of advancing the object into the vasculature. Furthermore, the structure used to deploy or disengage an object from its delivery system must not itself create problems which would traumatize the patient while the system is in the vasculature. In sum, it is important for a delivery system to function reliably and safely. It happens that several devices have been disclosed which are directed toward this result.

U.S. Pat. No. 3,902,501 which issued to Citron et al. for an invention entitled "Endocardial Electrode," and which is assigned to the same assignee as the present invention, discloses an interventional device for the deployment of a medical electrode. Specifically, the invention disclosed by Citron et al. incorporates a shroud which is axially fixed in its position on the device. As so positioned, the shroud overlaps and holds the exposed ends of the electrode's tines against the electrode body until the tines are to be deployed. To deploy the tines, a balloon on the electrode body is inflated to withdraw the tines from the shroud. Another example of this same basic deployment scheme, but for a slightly different application, is provided by U.S. Pat. No. 4,950,227 which issued to Savin et al. for an invention entitled "Stent Delivery System." According to the invention of Savin et al., a stent is positioned over the balloon of a balloon catheter. A pair of sleeves are axially fixed on the device with one end of each sleeve anchored to the catheter while the other end overlaps a respective end of the stent to hold the stent on the balloon. The result is that the sleeve is fixed at an axial location on the catheter. In an action similar to that disclosed for the device of Citron et al., when the balloon is inflated, the ends of the stent are withdrawn from their respective sleeve and the stent is thus deployed.

A difficulty not resolved by either the Citron et al. device or the Savin et al. device is the fact that the sleeves of Savin et al., like the shroud of Citron et al., are axially fixed and therefore substantially immobile. Stated differently, both of these devices rely solely on a change in the configuration of the object being deployed to disengage the object from the shroud or sleeves which hold the object against the balloon. Neither of these devices rely on a mechanical change in either the shroud or the stent for this disengagement. Thus, because the shroud (Citron et al.) or the sleeves (Savin et al.) do not mechanically withdraw axially from the tines or stent during deployment, less of the tines or stent can be covered by the respective shroud or sleeves than would otherwise be possible prior to deployment. Consequently, with less overlapping coverage, there is an increased risk of premature dislodgment of the object being deployed, and an increased risk of a system malfunction during deployment.

In light of the above it is an object of the present invention to provide a system for selectively holding a stent on a balloon delivery catheter which incorporates retainers that will mechanically shorten with an inflation of the balloon to facilitate disengagement of the stent from the system. Still another object of the present invention is to provide a system for selectively holding a stent on a balloon delivery catheter which effectively covers the projecting ends of a stent to protect the patient from snags, hang-ups or entanglements that might otherwise occur during advancement of the system into the vasculature of the patient. Yet another object of the present invention is to provide a system for selectively holding a stent on a balloon delivery catheter which includes stent retainers that revert to a low profile after stent deployment to facilitate withdrawal of the system from the vasculature of the patient. Another object of the present invention is to provide a system for selectively holding a stent on a delivery catheter which is relatively easy to manufacture, simple to use and comparatively cost effective.

SUMMARY OF THE PREFERRED EMBODIMENTS

In accordance with the present invention, a system for selectively holding a stent on a balloon delivery catheter includes both a proximal retainer and a distal retainer which respectively interact with the proximal end and the distal end of the stent. During advancement of the system into the vasculature of a patient, and prior to deployment of the stent, the retainers are used to hold the stent on the catheter. During actual deployment of the stent, however, as the balloon is being inflated the retainers are designed to mechanically withdraw from the stent and thereby facilitate disengagement of the stent from the system. Finally, after deployment of the stent, the retainers collapse with the deflated balloon to provide a low profile for the system during its withdrawal from the patient's vasculature.

In accordance with the present invention a stent is initially positioned over the central, or working, portion of an elongated inflatable balloon. Each of the retainers is then positioned over a respective cone at the ends of the balloon and each retainer has one end which is anchored to the catheter, the other, unanchored end is then positioned to overlap an end of the stent. For example, the proximal end of the proximal retainer is anchored, or bonded, to the catheter, while the distal end of the proximal retainer overlaps the proximal end of the stent. Similarly, the distal end of the distal retainer is anchored to the catheter while the proximal end of the distal retainer overlaps the distal end of the stent.

The structure of both the proximal retainer and the distal retainer are essentially the same. Specifically, each retainer includes a first plurality of filaments which are woven together with a second plurality of filaments to create a braided tube. With this structure, when the retainer is mounted on the catheter, the first plurality of filaments are helically disposed with a positive pitch angle relative to the longitudinal axis of the catheter, and the second plurality of filaments are likewise helically disposed, but with a negative pitch angle. The overall result is that the retainer is axially movable whenever the retainer expands in response to an inflation of the balloon. More specifically, this movement is between a first configuration wherein the retainer has a first length, and a second configuration wherein the retainer has a shorter second length. During a transition from the first to the second configuration, both the positive and negative helical pitches are increased. Importantly, as indicated, the first length is longer than the second length.

In the operation of the system of the present invention, the stent with overlapping retainers is advanced into the vasculature of a patient. Once the stent is properly positioned for deployment in the vasculature, the balloon is inflated. Due to the inflation of the balloon, the stent is expanded by the working section of the balloon. At the same time, the retainers are expanded by the cones of the balloon. With this expansion, the helical pitch of filaments in both of the retainers is increased and the retainer is actually shortened in an axial direction. The combined effect of the expanding stent and the shortened retainers causes the retainers to withdraw from the stent and thereby disengage the stent from the system. Subsequently, upon deflation of the balloon, the retainers collapse with the balloon to facilitate withdrawal of the system from the vasculature, and thus leave the stent implanted at the desired position.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENT

Figure 1:
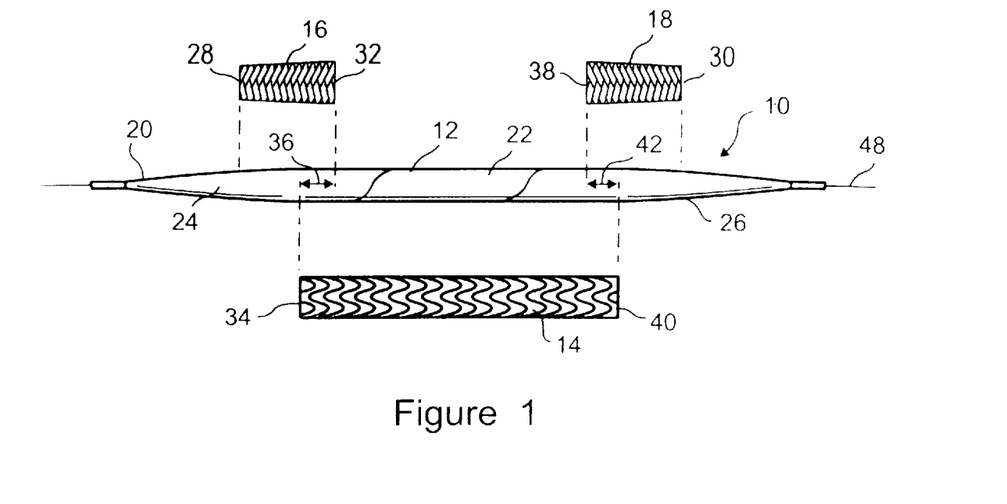
FIG. 1 is a side elevational view of the major components at the distal end of the stent delivery system of the present invention with the components separated from each other for clarity.

Referring initially to FIG. 1, a stent delivery balloon catheter system in accordance with the present invention is shown and generally designated 10. As shown in FIG. 1 the system 10 includes an elongated inflatable balloon 12 of a type well known in the pertinent art, a stent 14, a proximal retainer 16 and a distal retainer 18. More specifically, the balloon 12 is an integral part of a catheter 20 which is formed with an inflation lumen. The system 10 also includes a fluid pump (not shown) which is in fluid communication with the balloon 12 via the inflation lumen. Thus, as intended for the present invention, the fluid pump can be activated to either inflate or deflate the balloon 12.

As indicated in FIG. 1, the balloon 12 has a working section 22 which is intermediate a proximal cone 24 and a distal cone 26. Although the balloon 12 is shown in an inflated configuration in FIG. 1, it is to be appreciated that the overall configuration of the balloon 12, and specifically the configurations of working section 22 and cones 24, 26, will be changed when the balloon 12 is deflated. As clearly set forth below, this change in configuration of the balloon 12 between an inflated and a deflated configuration is important to the operation of the system 10.

During the assembly of the system 10, the stent 14 is positioned over the working section 22 and located to surround the balloon 12. Additionally, the proximal retainer 16 is positioned over the proximal cone 24 to surround the balloon 12, and the distal retainer 18 is similarly positioned over the distal cone 26 of the balloon 12. More specifically, in the initial assembly of the system 10 the balloon 12 is deflated. With the balloon 12 deflated, the stent 14 is positioned over the working section 22 and held against the balloon 12 in a manner well known in the pertinent art, such as by crimping. Once the stent 14 is in place on the balloon 12, the retainers 16, 18 are properly attached to the system 10. To do this, the proximal end 28 of proximal retainer 16 is anchored to the catheter 20 in a manner well known in the pertinent art, such as by heat bonding to the balloon 12. Likewise, the distal end 30 of distal retainer 18 is anchored to the catheter 20. It can be noted that the balloon 12 of the system 10 is, in all important respects, a conventional angioplasty balloon. No specific materials are required, and no specific dimension or configuration for the working section 22 or the cones 24, 26 are required.

FIG. 1 also shows that, due to their relative lengths and the selected anchor points where the retainers 16, 18, are attached to the catheter 20, when the stent 14 and the two retainers 16, 18 have been positioned on the balloon 12 there will be some overlap between these components of the system 10. Specifically, the distal end 32 of proximal retainer 16 will overlap the proximal end 34 of stent 14 by a distance 36. Similarly, the proximal end 38 of distal retainer 18 will overlap the distal end 40 of stent 14 by a distance 42. The exact magnitude of the distances 36, 42 are a matter of design choice, but they should be selected with the capabilities of the respective retainers 16 and 18 in mind. An appreciation of these capabilities will, perhaps, be best obtained by reference to FIG. 2.

Figure 2:
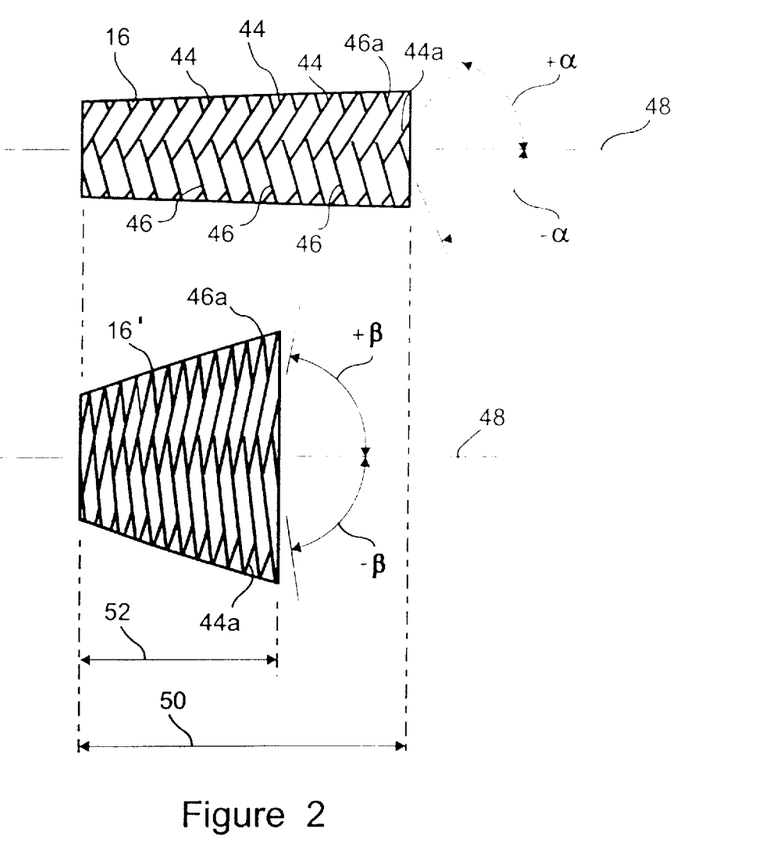
FIG. 2 is a comparison view of the braid component of a stent retainer according to the present invention with the retainer shown in an elongated configuration and in a compressed configuration.

In FIG. 2, the proximal retainer 16 is used as an example and is shown in two configurations. The configuration for retainer 16 shown in the upper part of the drawing corresponds to the condition wherein balloon 12 is deflated. On the other hand, the configuration for retainer 16' which is shown in the lower part of the drawing corresponds to the condition wherein balloon 12 is inflated. The capability for retainer 16 to move between these two configurations is, in large part, due to the structure of the retainer 16. As shown, the retainer 16 includes a first plurality of juxtaposed filaments 44. Also shown is a second plurality of juxtaposed filaments 46 which are interwoven with the filaments 44 to create a braided tube-like structure. It is to be appreciated that in this braided condition, the filaments 44 and the filaments 46 each assume a generally helical configuration which can be characterized by a pitch angle. For this purpose, consider the filament 44a as an example of the first plurality of filaments 44, and the filament 46a as an example of the second plurality of filaments 46. When the balloon 12 is deflated, it will be seen that the filaments 44 establish a positive pitch angle +α relative to an axis 48 and the filaments 46 establish a negative pitch angle −α relative to the axis 48. For purposes of the present invention, the axis 48 is taken to be the longitudinal axis defined by the retainer 16, 18. Incidentally, when the retainers 16, 18 are mounted on the catheter 20, axis 48 will also be the longitudinal axis of the catheter 20.

When the balloon 12 is inflated, the filaments 44, 46 will move, the pitch angle of the filaments will change, and the retainer 16 will assume the general configuration shown in FIG. 2 for retainer 16'. For the retainer 16' shown in FIG. 2, it is to be appreciated that, when the balloon 12 is inflated the filament 44a will establish a positive pitch angle +β and that the filament 46a will establish a negative pitch angle −β. Importantly, the pitch angles ±α are smaller than the pitch angles ±β. As a consequence of this change in configuration, the length 50 of the proximal retainer 16 (with balloon 12 deflated) is longer than the length 52 of the proximal retainer 16' (with balloon 12 inflated). For the present invention, the filaments 44, 46 can be made of filaments, or groups of filaments (yarn), and be of any metallic or plastic material in either a monofilament or multi-filament configuration, or in general, any material deemed suitable for the application thus described herein, such as nylon monofilament, stainless steel wire, glass fibers or an elastomer impregnated with a material such as graphite for enhanced lubricity. A suitable elastomer for this purpose is a PolyEther Block Amide (PEBA) available under the name PEBAX®, obtainable from the Elf ATOChem Corporation, Philadelphia, Pa. (e.g. PEBAX 5533). In any case, the significance of the interactions between filaments 44, 46 during the shortening of the retainer 16, 18 may be best appreciated by considering the operation of the system 10.

Figure 3A:
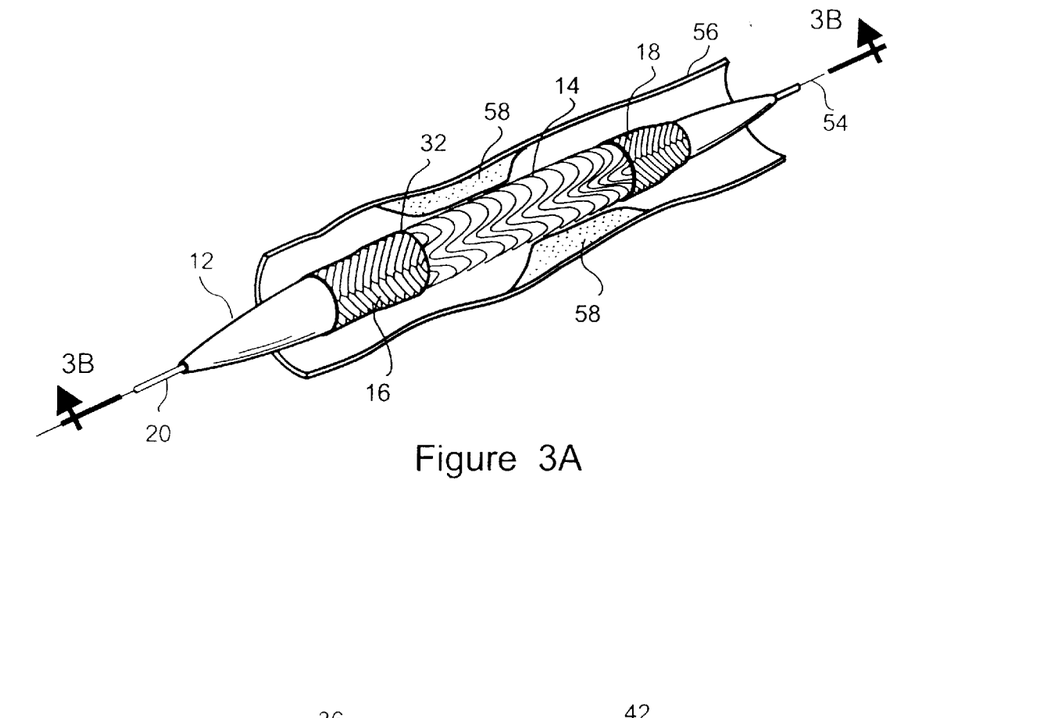
FIG. 3A is a view of the stent delivery system of the present invention inserted into a vessel within a stenosis in the vasculature of a patient prior to inflation of the balloon for deployment of the stent.
Figure 3B:
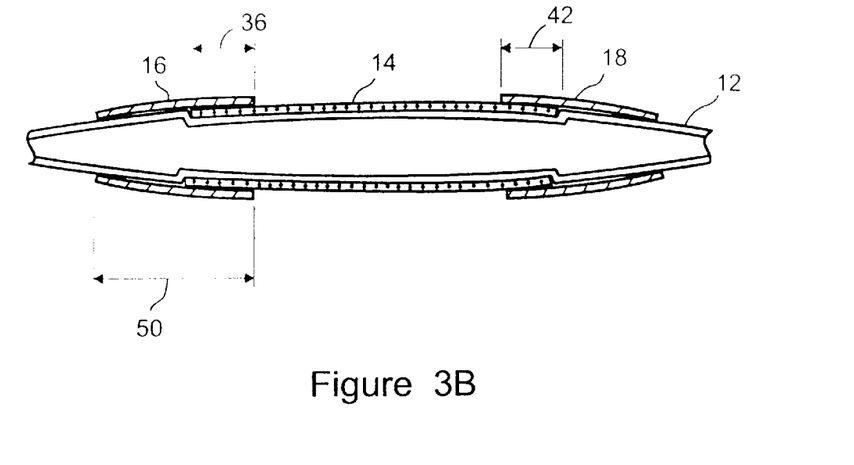
FIG. 3B is a cross-sectional view of the stent delivery system in the configuration shown in FIG. 3A.

In the operation of the system 10 of the present invention, the catheter 20 is advanced over a guidewire 54 into a vessel 56 of a patient's vasculature. Specifically, the catheter 20 is advanced into the vasculature until the stent 14 is positioned across the stenosis 58, or some type of obstruction or lesion in the vessel 56, where it is to be deployed (see FIG. 3A). Prior to deployment of the stent 14, the dimensional relationships between the stent 14, the proximal retainer 16 and the distal retainer 18 are, perhaps, best seen in FIG. 3B.

Figure 4A:
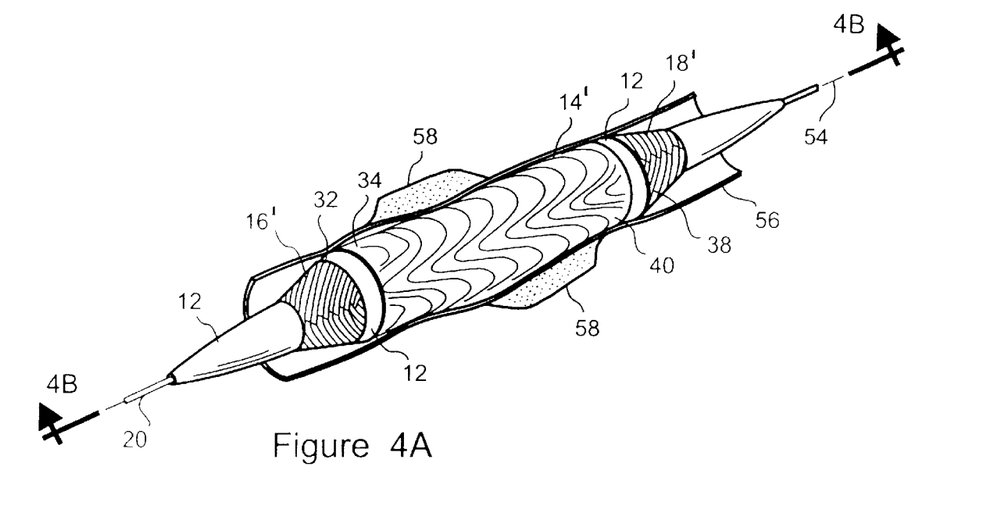
FIG. 4A is a view of the stent delivery system shown in FIG. 3A with the balloon inflated to deploy the stent.
Figure 4B:
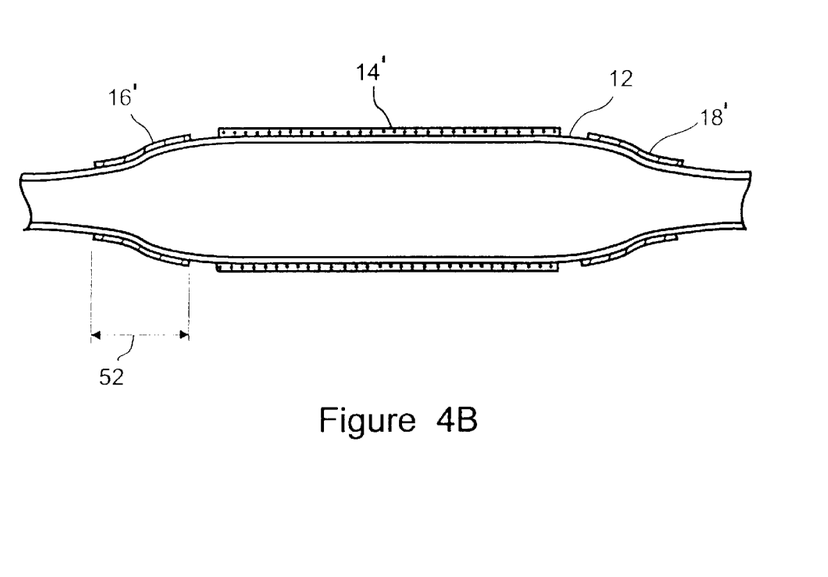
FIG. 4B is a cross-sectional view of the stent delivery system in the configuration shown in FIG. 4A.

Once the stent 14 is properly positioned, the balloon 12 is inflated to expand the stent 14' to a configuration, as shown in FIG. 4A. As is well known, this allows the stent 14' to act as a support structure for maintaining a patency in the vessel 56. For the present invention, and still referring to FIG. 4A, it should also be noted that the retainers 16', 18' have withdrawn from the stent 14'. Specifically, as previously disclosed with reference to FIG. 2, upon inflation of the balloon 12, the retainers 16, 18 are mechanically shortened by more than the respective overlap distances 36, 42. Thus, the retainers 16', 18' withdraw from the stent 14'. This separates the retainers 16', 18' from the stent 14' so that they no longer act to hold the stent 14' on the balloon 12. With deployment of the stent 14, the now-changed dimensional relationships between the stent 14', the proximal retainer 16' and the distal retainer 18' are best seen in FIG. 4B. After deployment of the stent 14', the balloon 12 is deflated.

Figure 5:
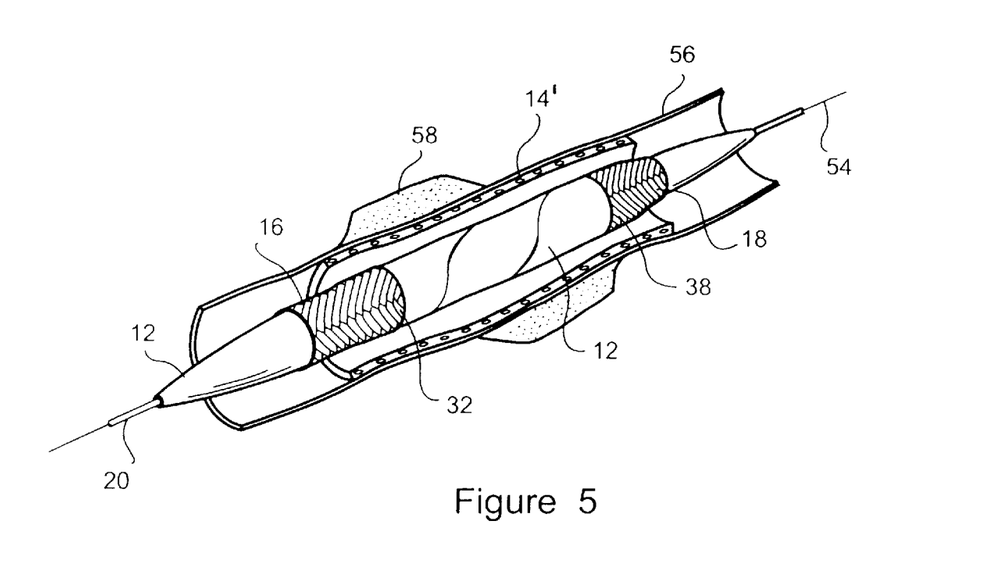
FIG. 5 is a view of the stent delivery system shown in FIGS. 3A and 4A after the stent has been deployed and the balloon deflated for withdrawal from the vasculature, the stent is shown in cross-section for clarity.

Upon deflation of the balloon (see FIG. 5) the expanded stent 14' will retain its expanded configuration and will be separated from the system 10. Thus, the expanded stent 14' remains in situ. The retainers 16' 18', however, no longer cooperate with the stent 14 and they therefore collapse with the balloon 12 as it returns to its deflated configuration. They do not reengage with the stent 14' and, accordingly, the retainers 16, 18 release the expanded stent 14' from the system 10. As can then be appreciated with reference to FIG. 5, after balloon 12 has been deflated, the balloon 12 and the retainers 16, 18 are withdrawn from vessel 56 of the patient's vasculature. As will be appreciated by the skilled artisan, the collapse of the retainers 16, 18 can be caused by biasing the retainers 16, 18 toward their collapsed configuration. This can be accomplished in several ways, such as by specifically weaving the filaments 44, 46 in a manner to generate the bias, or by use of a biasing sleeve 60 which can be incorporated into the retainer 16, 18.

Figures 6, 7B, 7C, 7D:
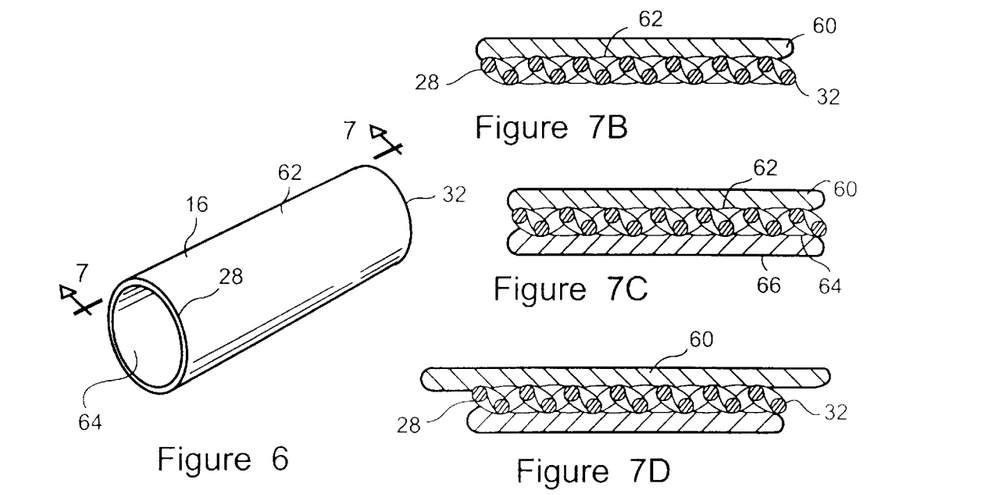
FIG. 6 is a perspective view of a stent retainer of the present invention.
FIGS. 7A–H are each a cross sectional view of various embodiments for the stent retainer of the present invention as seen along the line 7–7 in FIG. 6.

In FIG. 6, an exemplary retainer 16 is shown for purposes of disclosing possible embodiments for the retainer 16 which incorporate a biasing sleeve 60. As shown in FIG. 6, the retainer 16 is generally tubular shaped. With this shape the retainer 16 will have both an outer surface 62 and an inner surface 64. As will be appreciated by the skilled artisan, either or both surfaces 62, 64 can be entirely or partially covered by a biasing sleeve. Further, it will be appreciated that the retainer 16 can be divided into longitudinal segments which may, or may not, include braided filaments 44, 46. Several possibilities are shown in FIGS. 7A–H.

Figure 7A:
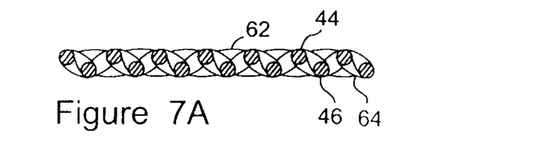
Figure 7E:
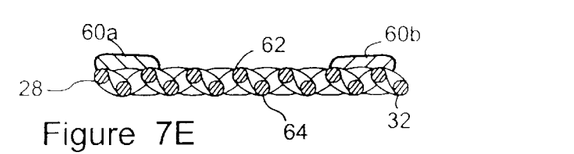
Figure 7F:
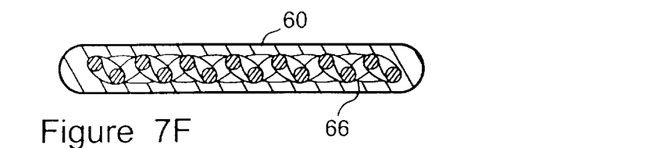
Figure 7G:
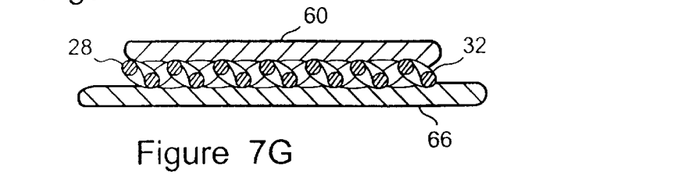
Figure 7H:
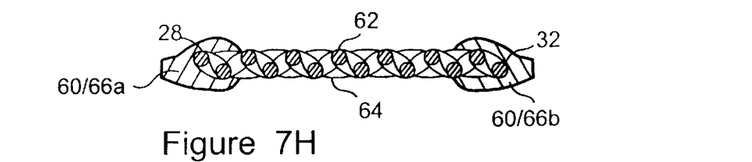

FIG. 7A illustrates an embodiment for the retainer 16 wherein there is only the filaments 44, 46 and no additional structure. For this embodiment, the collapsing bias of the retainer 16 must be provided by the filaments 44, 46 themselves. For the embodiment of retainer 16 shown in FIG. 7B, however, a biasing sleeve 60 is shown which covers the entire outer surface 62. For this embodiment, as with all other embodiments which incorporate biasing sleeves, it is to be appreciated that the sleeves 60 not only bias the retainer 16, 18 to return to its original tubular shape, they also provide the patient with some protection against abrasions which may be caused the structure of the filaments 44, 46. With the addition of a biasing sleeve 66 over the entire inner surface 64, the retainer 16 assumes the embodiment shown in FIG. 7C. For another embodiment, FIG. 7D shows that the sleeve 60 may extend past the proximal end 28 and past the distal end 32 of the retainer 16. In FIG. 7E, the sleeve 60 is shown to be bifurcated in order to cover proximal end 28 with only a sleeve portion 60a and to cover distal end 32 with only a sleeve portion 60b. The embodiment of FIG. 7F shows an embodiment wherein the sleeve 60 on the outer surface 62 is integral with the sleeve 66 on the inner surface 64. For this embodiment, the filaments 44, 46 are effectively embedded between the sleeves 60, 66. The embodiment of FIG. 7G is similar to that shown in FIG. 7D, with the difference being that the sleeve 66 on inner surface 64 extends beyond the proximal end 28 and the distal end 32, and not vice versa. Finally, the embodiment for the retainer 16 shown in FIG. 7H shows an integral connection between sleeve portions 60/66a at the proximal end 28 of retainer 16, and sleeve portions 60/66b at the distal end 32 of the retainer 16. It will be appreciated that still other variations in the embodiments of retainers 16, 18 are possible.

Figure 8:
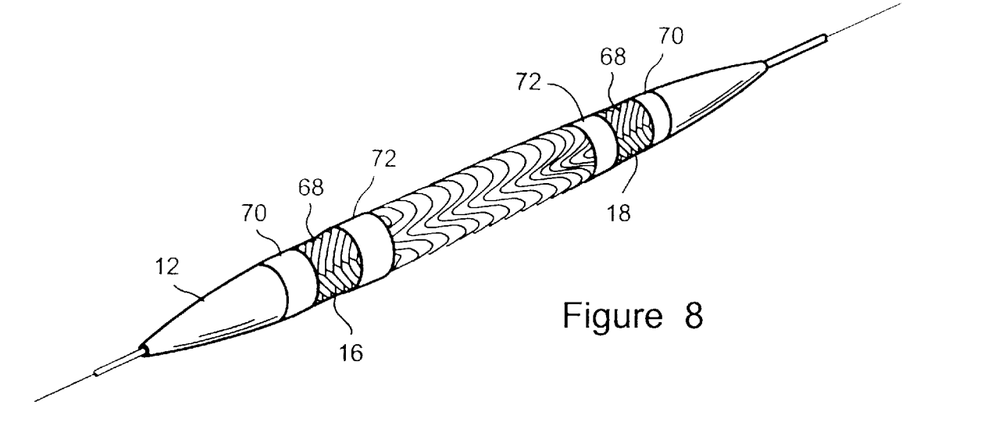
FIG. 8 is a perspective view of the stent delivery system of the present invention employing an alternate embodiment for the retainers.

FIG. 8 shows the system 10 of the present invention incorporating the particular embodiment for retainers 16, 18 that is depicted in FIG. 7H. As shown in FIG. 8, each of these retainers 16, 18 has a segment 68 which includes braided filaments 44, 46. For this particular embodiment, however, the segment 68 of the braided filaments 44, 46 is bonded between extensions 70 and 72 of the sleeve 66. As can be appreciated by the skilled artisan, these extensions 70, 72 can be made of an elastomeric material, such as a PEBAX® material disclosed above.

While the particular Method Of Stent Retention To A Delivery Catheter Balloon-Braided Retainers as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A system for selectively holding a stent on a delivery catheter which comprises:

an inflatable balloon defining a longitudinal axis;

a first plurality of mutually juxtaposed filaments;

a second plurality of mutually juxtaposed filaments woven with said first plurality of filaments to create a retainer having a proximal end and a distal end with a length therebetween;

means for anchoring said proximal end of said retainer to said balloon to position said distal end of said retainer over a proximal portion of said stent when said stent is mounted on said balloon to hold said stent against said balloon, said retainer being positioned with said filaments of said first plurality helically disposed with a positive pitch relative to said axis and said filaments of said second plurality helically disposed with a negative pitch relative to said axis; and means for inflating said balloon to urge said balloon against said retainer to increase said positive pitch and increase said negative pitch of respective said filaments to shorten said length of said retainer to withdraw said retainer from said stent to release said stent from said balloon.

2. A system as recited in claim 1 further comprising:

a second retainer having a proximal end and a distal end with a length therebetween; and means for anchoring said distal end of said second retainer to said balloon to position said proximal end of said second retainer over a distal portion of said stent when said stent is mounted on said balloon, said second retainer including a first plurality of filaments having a positive pitch and a second plurality of filaments having a negative pitch, with said positive pitch and said negative pitch of respective said filaments being increased by inflation of said balloon to shorten said length of said second retainer to withdraw said second retainer from said stent to release said stent from said balloon.

3. A system as recited in claim 1 wherein said retainer has an inner surface and an outer surface, and wherein said system further comprises an elastomeric sleeve covering at least a portion of said outer surface, said sleeve being biased by inflation of said balloon to decrease said positive pitch and to decrease said negative pitch of respective said filaments to lengthen said retainer and collapse said balloon to separate said retainer and said balloon from said stent after said stent is deployed and said balloon is deflated.

4. A system as recited in claim 1 wherein said retainer has an inner surface and an outer surface, and wherein the system further comprises an elastomeric sleeve positioned against at least a portion of said inner surface, said sleeve being biased by inflation of said balloon to decrease said positive pitch and to decrease said negative pitch of respective said filaments to lengthen said retainer and collapse said balloon to separate said retainer and said balloon from said stent after said stent is deployed and said balloon is deflated.

5. A system as recited in claim 1 wherein said retainer has an inner surface and an outer surface, and wherein the system further comprises a first elastomeric sleeve positioned against at least a portion of said outer surface and a second elastomeric sleeve positioned against at least a portion of said inner surface, said first and second sleeves being biased by inflation of said balloon to act in concert to decrease said positive pitch and to decrease said negative pitch of respective said filaments to lengthen said retainer and collapse said balloon to separate said retainer and said balloon from said stent after said stent is deployed and said balloon is deflated.

6. A system as recited in claim 1 wherein said filaments are each made of an impregnated elastomer to make said filaments lubricious.

7. A system as recited in claim 1 wherein said filaments are each made of a metallic material.

8. A system as recited in claim 1 wherein said filaments are each made of a composite including an elastomeric material PEBAX 5533 with approximately twenty five percent graphite.

9. A stent delivery balloon catheter system which comprises: an inflatable balloon having a first end and a second end with a working section therebetween, said balloon defining a longitudinal axis;

a stent having a first end and a second end, said stent being positioned on said balloon over said working section; and a tubular shaped retainer having a first end and a second end and being mechanically moveable between a first configuration wherein said retainer has a first surface length and a second configuration wherein said retainer has a second surface length, said first surface length being greater than said second surface length, and further wherein said retain has said first end thereof anchored to said catheter and said second end thereof overlaps a portion of said stent to hold said stent on said balloon while said balloon is deflated and said retainer is in said first configuration, said second end of said retainer withdrawing from said stent to release said stent from said catheter when said balloon is inflated to move said retainer into said second configuration.

10. A system as recited in claim 9 wherein said balloon defines a longitudinal axis and said retainer comprises:

a first plurality of mutually juxtaposed filaments; and a second plurality of mutually juxtaposed filaments woven with said first plurality of filaments to create a braided tube, said tube being positioned with said filaments of said first plurality helically disposed with a positive pitch relative to said axis and said filaments of said second plurality helically disposed with a negative pitch relative to said axis, there being an increase in said positive pitch and an increase in said negative pitch of respective said filaments when said retainer moves from said first configuration to said second configuration.

11. A system as recited in claim 10 wherein said braided tube has an inner surface and an outer surface, and wherein said system further comprises an elastomeric sleeve covering at least a portion of said outer surface, said sleeve being biased by inflation of said balloon to return said retainer from said second configuration to said first configuration to lengthen said tube and collapse said balloon to separate said tube and said balloon from said stent after said stent is deployed and said balloon is deflated.

12. A system as recited in claim 10 wherein said braided tube has an inner surface and an outer surface, and wherein said retainer further comprises an elastomeric sleeve positioned against at least a portion of said inner surface, said sleeve being biased by inflation of said balloon to return said retainer from said second configuration to said first configuration to lengthen said tube and collapse said balloon to separate said tube and said balloon from said stent after said stent is deployed and said balloon is deflated.

13. A system as recited in claim 10 wherein said braided tube has an inner surface and an outer surface, and wherein said retainer further comprises a first elastomeric sleeve positioned against at least a portion of said outer surface and a second elastomeric sleeve position against at least a portion of said inner surface, said first and second sleeves being biased by inflation of said balloon to act in concert to return said retainer from said second configuration to said first configuration to lengthen said tube and collapse said balloon to separate said tube and said balloon from said stent after said stent is deployed and said balloon is deflated.

14. A stent delivery balloon catheter system which comprises:

an inflatable balloon having a proximal cone and a distal cone with a working section therebetween;

a stent having a proximal end and a distal end, said stent being positioned on said balloon over said working section;

a proximal retainer having a proximal end and a distal end with said proximal end thereof anchored to said balloon to position said proximal retainer over said proximal cone of said balloon and position said distal end thereof in an overlapping relationship with said proximal end of said stent, said proximal retainer having a surface length;

a distal retainer having a proximal end and a distal end with said distal end thereof anchored to said balloon to position said distal retainer over said distal cone of said balloon and position said proximal end thereof in an overlapping relationship with said distal end of said stent, said distal retainer having a surface length; and means for inflating said balloon to mechanically shorten said respective surface lengths of said proximal retainer and said distal retainer to release said stent from said system as said stent is deployed by inflation of said balloon.

15. A system as recited in claim 14 wherein said proximal retainer and said distal retainer are respectively moveable between a first configuration wherein each said retainer has a first length, and a second configuration wherein each said retainer has a second length, said first length being greater than said second length, and further wherein each said retainer has a first end thereof anchored to said catheter and a second end thereof overlapping a portion of said stent to hold said stent on said balloon while said balloon is deflated and each said retainer is in said first configuration, said second end of each said retainer withdrawing from said stent to release said stent from said catheter when said balloon is inflated to move each said retainer into said second configuration.

16. A system as recited in claim 15 wherein said balloon defines a longitudinal axis and each said retainer comprises:

a first plurality of mutually juxtaposed filaments; and a second plurality of mutually juxtaposed filaments woven with said first plurality of filaments to create a braided tube, said tube being positioned with said filaments of said first plurality helically disposed with a positive pitch relative to said axis and said filaments of said second plurality helically disposed with a negative pitch relative to said axis, there being an increase in said positive pitch and an increase in said negative pitch of respective said filaments when said retainer moves from said first configuration to said second configuration.

17. A system as recited in claim 16 wherein said braided tube has an inner surface and an outer surface, and wherein said system further comprises an elastomeric sleeve covering at least a portion of said outer surface, said sleeve being biased by inflation of said balloon to return said retainer from said second configuration to said first configuration to lengthen said tube and collapse said balloon to separate said tube and said balloon from said stent after said stent is deployed and said balloon is deflated.

18. A system as recited in claim 16 wherein said braided tube has an inner surface and an outer surface, and wherein said retainer further comprises an elastomeric sleeve positioned against at least a portion of said inner surface, said sleeve being biased by inflation of said balloon to return said retainer from said second configuration to said first configuration to lengthen said tube and collapse said balloon to separate said tube and said balloon from said stent after said stent is deployed and said balloon is deflated.

19. A system as recited in claim 16 wherein said braided tube has an inner surface and an outer surface, and wherein said retainer further comprises a first elastomeric sleeve positioned against at least a portion of said outer surface and a second elastomeric sleeve position against at least a portion of said inner surface, said first and second sleeves being biased by inflation of said balloon to act in concert to return said retainer from said second configuration to said first configuration to lengthen said tube and collapse said balloon to separate said tube and said balloon from said stent after said stent is deployed and said balloon is deflated.

20. A system as recited in claim 16 wherein said filaments are made of a material selected from the group consisting of nylon monofilament, stainless steel wire and PEBAX 5533 with approximately twenty five percent graphite.

* * * * *

UNITED STATES PATENT AND TRADEMARK OFFICE
CERTIFICATE OF CORRECTION

PATENT NO. : 6,183,505 B1
DATED : February 6, 2001
INVENTOR(S) : Mohn Jr. et al.

It is certified that error appears in the above-identified patent and that said Letters Patent is hereby corrected as shown below:

Column 9,
Line 48, after "length;" insert -- and --;
Line 54, delete "; and" and insert -- , -- therefor;
Line 55, delete "means for inflating said balloon to mechanically shorten" and insert -- wherein when said balloon is inflated, --; and
Line 57, after "said distal retainer", insert -- mechanically shorten --.

Signed and Sealed this

Twentieth Day of November, 2001

Attest:

*Nicholas P. Godici*

NICHOLAS P. GODICI
*Attesting Officer*  *Acting Director of the United States Patent and Trademark Office*